(12) United States Patent
Bergquist

(10) Patent No.: US 6,239,335 B1
(45) Date of Patent: May 29, 2001

(54) SYNTHETIC CORN HYBRID P89

(75) Inventor: Richard R. Bergquist, El Paso, IL (US)

(73) Assignee: Optimum Quality Grains, L.L.C., Johnston, IA (US)

(*) Notice: Subject to any disclaimer, the term of this patent is extended or adjusted under 35 U.S.C. 154(b) by 0 days.

(21) Appl. No.: 09/328,036

(22) Filed: Jun. 8, 1999

(51) Int. Cl.⁷ .............. A01H 5/00; A01H 4/00; A01H 1/00; C12N 5/06
(52) U.S. Cl. .......... 800/320.1; 800/298; 800/275; 800/271; 800/268; 800/266; 800/264; 435/412; 435/424; 435/430; 435/430.1
(58) Field of Search .................. 800/320.1, 298, 800/275, 268, 266, 264; 435/412, 424, 430, 430.1

(56) References Cited

U.S. PATENT DOCUMENTS

| | | |
|---|---|---|
| 5,675,065 | 10/1997 | Bergquist . |
| 5,704,160 | 1/1998 | Bergquist et al. . |
| 5,706,603 | 1/1998 | Bergquist et al. . |
| 5,763,756 | 6/1998 | Bergquist . |
| 5,824,854 | 10/1998 | Bergquist . |
| 5,824,855 | 10/1998 | Bergquist . |
| 5,850,031 | 12/1998 | Bergquist . |
| 5,900,528 | 5/1999 | Bergquist . |
| 5,907,089 | 5/1999 | Bergquist . |
| 5,922,934 | 7/1999 | Bergquist . |
| 5,936,143 | 8/1999 | Bergquist . |

*Primary Examiner*—Gary Benzion
(74) *Attorney, Agent, or Firm*—Bullwinkel Partners, Ltd.

(57) ABSTRACT

A synthetic hybrid corn plant having the designation P89, produced by crossing two proprietary Optimum Quality Grain, L.L.C. maize synthetics, P90A-Reid and P91B-Lancaster. P89 has the unique property of imparting high oil levels in the grain of certain normal and male sterile hybrids when used as a pollinator. P89 is characterized by excellent cold tolerant seedling vigor for rapid emergence in cold soils and excellent late-season adaptability facilitating nicking with medium-late maize hybrids to condition fast dry-down and superior grain quality in the grain arising from the recipient female grain parent. This invention thus relates to the seeds, plants and plant parts of P89, to plants regenerated from tissue culture of the plants or plant parts of P89, to a method of producing P89, and to a method for producing grain using P89 as a pollinator.

15 Claims, No Drawings

SYNTHETIC CORN HYBRID P89

FIELD OF THE INVENTION

This invention is in the field of plant breeding. Specifically, this invention relates to a novel synthetic corn hybrid having the designation P89 and useful in the proprietary TOPCROSS® grain production system described in U.S. Pat. Nos. 5,704,160 and 5,706,603 by Bergquist et al.

BACKGROUND OF THE INVENTION

Uses of Corn

Corn (Zea mays L.) is an important crop used as a human food source, animal feed, and as a raw material in industry. The food uses of corn, in addition to the human consumption of corn kernels, include products of both the dry milling and wet milling industries. The principal products of dry milling include grits, meal and flour. The principal products of wet milling include starch, syrups, and dextrose. A by-product of both dry and wet milling is corn oil, which is recovered from corn germ. As animal feed, corn is used primarily as a feedstock for beef cattle, dairy cattle, swine, poultry, and fish.

Industrial uses of corn mainly consist of the use of corn starch produced by wet milling and corn flour produced by dry milling and the whole kernel fermentation for production of foodgrade and industrial use ethanol. The industrial applications of corn starch and flour are based on their functional properties, such as viscosity, film formation ability, adhesiveness, absorbent properties and ability to suspend particles. Corn starch and flour are used in the paper and textile industries, and as components in adhesives, building materials, foundry binders, laundry starches, sanitary diapers, seed treatments, explosives, and oil-well muds. Plant parts other than the corn kernels are also used in industry. For example, stalks and husks can be made into paper and wallboard, and corn cobs can be used for fuel and to make charcoal.

Principles of Conventional Plant Breeding

The majority of the commercial corn produced in the United States is produced from hybrid seed. The production of hybrid seed first requires the development of elite corn inbred lines that possess good combining ability to produce agronomically superior hybrids. The majority of hybrid seed produced in the United States is of the single cross type, wherein two inbred lines are intermated, or crossed, to produce what is termed an $F_1$ single cross hybrid. The resulting kernels from this intermating are then sold as seed to commercial growers who plant the seed and harvest the second generation, or $F_2$ grain, for use on farm or for commercial sale.

The production of a conventional single cross hybrid seed involves controlling the direction of pollination from one inbred to the other to assure the production of predominantly hybrid (cross pollinated) seed. Typically, directed pollination is accomplished by interplanting separate rows of female corn plants with male corn plants. The female corn plants that are male sterile may be produced by genetic mechanisms which render the corn tassel nonfunctional or by detasseling the plants in the field.

The development of corn hybrids requires the development of homozygous inbred lines or uniform synthetic populations of unique heterotic background, the crossing of these lines or synthetic populations, and evaluation of test crosses. Pedigree breeding and recurrent selection breeding programs are used to develop inbred lines and synthetic populations from breeding populations. Breeding programs combine desirable traits from two or more inbred lines or various broad-based sources into breeding pools from which new inbred lines or synthetic populations are developed by inbreeding or random mating and selection of desired phenotypes. The new inbreds and/or synthetic lines are crossed with other inbred lines and/or synthetic populations and the hybrids from these crosses are evaluated to determine which have commercial value and agronomic usefulness.

Pedigree breeding starts with the crossing of two genotypes, each of which may have one or more desirable characteristics that is lacking in the other or which complements the other. If the two original genotypes do not provide all of the desired characteristics, other sources can be included during the breeding. In the pedigree breeding method, superior plants are selfed or random mated and the resulting seed selected in successive generations. Pedigree records of ancestry are carefully maintained for each family and ear row selection through succeeding generations. In the succeeding generations, the heterozygous condition of the corn germplasm gives way to homozygous true breeding lines as a result of inbreeding and selection. Typically, in the pedigree method of breeding, five or more generations of inbreeding and selection is practiced.

Backcrossing can be used to improve an inbred line by transferring a specific desirable trait from one inbred or source to another inbred that lacks that trait. This can be accomplished, for example, by first crossing a superior inbred (recurrent parent) to a donor inbred (nonrecurrent parent). The donor inbred carries (donates) the appropriate gene(s) for the desired trait to the next generation. After five or more backcross generations with selection for the desired trait, the inbred will be heterozygous for loci controlling the characteristic being transferred, but will be like the superior parent for most or almost all other genes. The last backcross generation can be selfed to produce a pure breeding progeny for the gene(s) being transferred.

An important consequence of the homozygosity and homogeneity of the inbred lines is that the hybrid between any two inbreds will always be the same. Once the inbreds or synthetics that give the best hybrid have been identified, the hybrid seed can be reproduced indefinitely as long as the homogeneity of the inbred or synthetic parents is maintained.

As previously noted, a single cross hybrid is produced when two unrelated inbred or synthetic lines are crossed to produce the $F_1$ progeny. A three-way cross hybrid is produced from three inbred lines (or synthetics) where two of the inbred lines (or synthetics) are crossed (A×B) and then the resulting $F_1$ hybrid is crossed with the third inbred (or synthetics) (A×B)×C. A double cross hybrid is produced from four inbred lines (or synthetics) by crossing pairs (A×B) and (C×D) and then crossing the two $F_1$ hybrids (A×B)×(C×D).

Much of the hybrid vigor exhibited by $F_1$ hybrids is lost in the next generation ($F_2$). Consequently, seed (grain) from hybrid varieties is not used for planting stock.

The objective of typical plant breeding is to combine in a single variety/hybrid the desirable traits of the parental lines. For field crops such as corn, these desirable traits may include resistance to diseases, insects, herbicide tolerance, and tolerance to heat and drought, reducing time to crop maturity, and improved agronomic quality. With mechanical harvesting of many crops, uniformity of plant characteristics such as germination time and stand establishment, growth rate, and fruit/seed size are also desirable.

The problem with conventional breeding techniques is that there are several grain quality traits, such as high oil content, that cannot readily be combined in a high-yielding single cross hybrid. By contrast, synthetic hybrids, such as the one described herein, when used as a pollinator in the TOPCROSS® grain production system, can impart desirable grain quality characteristics, such as high oil content, to the resulting $F_1$ grain without a significant loss in yield.

Synthetic Varieties

A synthetic hybrid consists of an array of similar genotypes that were identified from intercross tests and bulked into a random mating population having a desired phenotype. The intercrosses between two different heterotic groups results in the continuous production of a specific synthetic hybrid of desired phenotype.

Corn has male flowers, located on the tassel, and female flowers, located on the ear, of the same plant. Because of this monoecy, corn plants can be bred by both self-pollination and cross-pollination techniques. Corn is self-pollinated if pollen from one flower is transferred to the same or another flower on the same plant. Corn is cross-pollinated if the pollen comes from a flower on a different plant.

Plants that have been self-pollinated and selected for uniform type over many generations become homozygous at almost all gene loci and produce a uniform population of true breeding progeny. Cross pollination between two homozygous lines produces a uniform population of hybrid plants that nevertheless may be heterozygous for many gene loci. A cross between two plants that are each heterozygous for a number of gene loci will produce a population of hybrid plants that differ genetically and will not be uniform.

Natural pollination occurs when wind blows pollen from tassels to silks that protrude from tops of the incipient ears on plants of the same genotype and different genotype, resulting in both self- and cross-pollination. When a population of genotypes are combined from all possible intercrosses among a number of selected genotypes and are allowed to open pollinate, the result is called a synthetic variety. A synthetic variety is made up of genotypes which previously have been tested for their ability to produce a superior progeny when crossed in all combinations.

Corn plants may be maintained as an outcrossing synthetic population that is much less homogeneous than a self-pollinated group. Every plant in such a group is certain to be heterozygous at many or most loci, and this heterozygosity must either be maintained during a breeding program or restored at the end of the program if productivity is to be satisfactory. The main requirement in maintaining a synthetic line is that a sufficient number of plants of heterozygous background be maintained to recover the gene frequencies that are desired for the synthetic population so as to prevent genetic drift toward undesired gene frequencies.

The Desirability of High Oil Content Grain

The concentration of oil in most varieties of corn ranges from less than 3.0% to 4.5% at 0% moisture. Embryos of ordinary corn can contain 30% oil, while embryos of high oil corn strains can contain as much as 50% oil and are much larger in size than ordinary corn embryos.

There are several reasons for wanting to develop a method for growing corn that is high in oil content. First, corn oil is a premium oil and regularly more valuable than starch, the other major component of corn kernels. Second, high oil corn possesses a higher available energy content than ordinary corn, and thus is a more valuable feed for poultry and livestock. In animal feeding trials it has been found that less high oil corn is required per unit of grain than is required with ordinary corn. In addition, high oil corn requires substantially less soybean meal to balance a typical animal diet, and may be used to replace oil containing additives in animal feed.

Additional impetus was given to breeding corn for high oil by the development of wide-line nuclear magnetic resonance spectroscopy (NMR) and near-infrared spectroscopy (NIR) as analytical tools for the nondestructive analysis of bulk or single kernel samples that can be carried out in as little as two seconds. The development of such tools made it much easier and much quicker to determine the oil content of grain, thereby encouraging experimentation in the area of breeding for high oil.

Thus there exists at present a growing market for corn having high oil, increased protein and other special end-use properties which is not met by corn of standard composition. The diverse types of corn available to plant breeders provides a potential for modification of quality and quantity of grain protein, starch, and oil. Corn now can be developed to more precisely meet the specific nutritional requirements of animals or to meet particular industrial needs.

The Topcross® Grain Production System

Unfortunately, high oil is a property that cannot readily be achieved in a high yielding single-cross hybrid. This is because oil content, while being a moderately heritable trait, is influenced by a series of oil genes that have additive effects on oil content and occur at a complex of loci in at least eight linkage groups that influence the amount of oil in the grain progeny. obtaining a hybrid having all or most of these oil genes can take many years of breeding. Further increasing the difficulty of breeding for high oil content is the fact that the grain yield of higher oil hybrids is generally inferior when compared to elite dent corn hybrids.

A method of producing a high yield of corn having high oil content without requiring years of breeding is described in Bergquist et al. U.S. Pat. No. 5,704,160. The primary aspect of this method, known as the TOPCROSS® grain production system, is the interplanting of a pollinator corn plant possessing the characteristics for significantly increasing oil and protein levels in the resulting grain with a male sterile hybrid corn plant. The resulting grain possesses an oil content much higher than would be expected for self- or cross-pollination of the fertile version of the hybrid corn plant.

In practice, the seed of the pollinator with improved grain quality traits is blended in small amounts with seed of an elite male sterile grain parent hybrid, but with sufficient pollinator seed to permit abundant pollen production for fertilization of the male sterile grain parent hybrid. The relatively low ratio of pollinator seed to male sterile grain parent seed (less than one pollinator plant to every three grain parent plants) takes advantage of the higher grain yield potential of the elite grain parent hybrid while assuring a sufficient population of pollinator plants to pollinate the male sterile grain parent plants.

Need for Superior Pollinators

Critical to the success of the TOPCROSS® grain production system is the use of a pollinator capable of enhancing the grain quality traits of the $F_1$ offspring. To obtain such pollinators, the corn breeder must select and develop corn plants that have the traits that result in superior inbred and synthetic parental lines.

The pollinator for the TOPCROSS® grain production system need not be genetically homozygous (inbred) or even uniform in appearance, and need not be selected for genetic combining ability with female plants. However, the pollinator should have uniform desirable grain quality characteristics, such as high oil, that will influence the grain quality characteristics of the $F_1$ offspring, and the ability to pollinate the female plants. A hybrid obtained by crossing two synthetic populations of different heterotic backgrounds results in a synthetic hybrid with predictable heterozygosity and genetic variability among plants that is particularly useful as a male pollinator in blends with male sterile hybrid grain parents in the TOPCROSS® grain production system. Some genetic variability is desirable because it extends the flowering period of the pollinator. Synthetic corn hybrid P89 was developed to achieve these characteristics.

Advantages of Synthetic Hybrids

The use of synthetic hybrids (such as P89) as TOPCROSS® grain production system pollinators affords a number of advantages over the use of inbreds, hybrids produced from single crosses, or hybrids produced from three way crosses. For instance, synthetic hybrids can be developed more rapidly than commercial hybrids. Specifically, the use of a synthetic population can more rapidly establish stability of dominant oil genes, thus by-passing the many generations of inbreeding that is required to produce inbreds for making single cross hybrids.

Second, synthetic hybrids often have excellent vigor comparable to that of commercial hybrids. Inbreds, by contrast, typically lose vigor with each successive generation of inbreeding. This is an important advantage of synthetics because pollinator vigor is critical for ample pollen shed at the time of silking in the TOPCROSS® grain production system. Synthetic hybrid P89 expresses cold vigor in seedling growth stages greater than even most open pollinated synthetic populations.

Third, a synthetic variety, utilizing heterosis in which pollination control is a factor, is more likely to disperse pollen over a longer period of time than a single cross hybrid. The predictable greater variability of synthetic varieties as compared with single crosses permits more flexibility to meet the changing growing conditions typical of field production. In addition, because of the longer flowering period, fewer synthetic pollinators need be developed to be used in blends with many different grain parents.

Fourth, the synthetic hybrid pollinator is more easily produced during periods of heat and drought stress on dryland production than a single-cross hybrid using less vigorous inbred seed stocks. For example, in non-irrigated dryland field tests conducted during 1993 and 1994, production of synthetic hybrid seed remained relatively constant at about 55 bushels per acre despite the fact that rainfall accumulation during the critical months of May, June and July fell from 40.84 cm in 1993 to 13.82 cm in 1994. Over the same period, single cross seed production using inbred seed stocks fell to less than 25 bushels per acre in 1994 from 55 bushels per acre in 1993.

Fifth, the single cross synthetic hybrid pollinator which results from the cross of two parental synthetic populations, A×B, is more quickly produced in a single generation compared to a three-way cross pollinator (A×B)C that requires an additional plant generation to produce the hybrid three-way cross pollinator. For example, the A×B synthetic hybrid is simply produced in a single plant growing generation in the production of P89 single-cross synthetic hybrid while the three-way cross synthetic hybrid pollinator would require an additional plant generation to produce the final hybrid (A×B) crossed to the parental C-population to produce a synthetic three-way hybrid cross designated (A×B)C.

SUMMARY

According to the invention, there is provided a novel synthetic corn hybrid, designated P89, that when used to pollinate an elite male sterile hybrid grain parent, produces commercial grain exhibiting improved quality grain traits, including high oil. Furthermore, when P89 is used to pollinate male sterile hybrid grain parents that are harvested as whole plants at approximately 50% plant moisture, it produces commercial fodder that expresses improved feed efficiency and rate of weight gain.

P89 is characterized by excellent cold tolerant seedling vigor for rapid emergence in cold soils and excellent late-season adaptability facilitating nicking with late maize hybrids to condition fast dry-down and superior grain quality in the grain arising from the recipient female grain parent.

This invention thus relates to the seeds, plants and plant parts of P89, to plants regenerated from tissue culture of the plants or plant parts of P89, to a method of producing P89 by crossing P90A and P91B synthetics, and to a method for producing grain using P89 as a pollinator.

DEFINITIONS

In the description and examples that follow, a number of terms are used. In order to provide a clear and consistent understanding of the specification and claims, including the scope to be given such terms, the following definitions are provided:

Backcross. The cross of a hybrid to either one of its parents. The offspring of such a cross is referred to as the backcross generation.

Backcross Method of Breeding. A system of breeding carried out by several generations of backcrossing to one of the parents of a hybrid and subsequent selection. The characteristics of the recurrent parent are retained for the most part, and characteristics from the nonrecurrent parent are added.

Bulk Method of Breeding. The growing of segregating generations of a hybrid of self-pollinating crops in a bulk, with or without mass selection, followed by individual plant selection in $F_6$ or later generations.

Cytoplasmic Inheritance. Transmission of hereditary characteristics through the cytoplasm as distinct from transmission by genes carried by chromosomes in the nucleus. Detected by differing contribution of male and female parents in reciprocal crosses.

Donor parent. The parent from which one or a few genes are transferred to the recurrent parent in backcross breeding.

Ear Height. The ear height is a measure from the ground to the top developed ear node attachment and is measured in centimeters.

Early Stand Count. This is a measure of the stand establishment in the spring and represents the number of plants that emerge on a per-plot basis for the hybrid.

Elite. This term characterizes a plant or variety possessing favorable traits, such as, but not limited to, high yield, good grain quality and disease resistance.

Embryo. The rudimentary plant in a seed. The embryo arises from the zygote. In high oil corn breeding, increases in oil content are accompanied by increases in embryo size.

Endosperm. The nutritive tissue formed within the embryo sac in seed plants. It commonly arises following the fertilization of the two primary endosperm nuclei of the embryo sac by the two male sperms. In a diploid organism the endosperm is triploid.

Expressivity. The degree of manifestation of a genetic character.

$F_1$. The first generation of a cross.

$F_2$. The second filial generation obtained by self-fertilization or crossing inter se of $F_1$ individuals.

F₃. Progeny obtained by self-fertilizing F₂ individuals. Subsequent generations F₄, F₅, etc.

Field corn. Varieties or cultivars of corn grown extensively on large acreage within a broad but defined geographic area for the production of grain and/or forage.

GDD Shed. The GDD is the number of growing degree days (GDD) or heat units required for an inbred line or hybrid to reach anthesis or pollen shed from the time of planting. Growing degree days are calculated by the Barger Method, where the heat units for a 24-hour period are:

$$GDD = \frac{(Max.+Min.)}{2} - 50$$

The highest maximum used is 86 degrees F. and the lowest minimum used is 50 degrees F. For each hybrid it takes a certain number of GDDs to reach various stages of plant development. GDDs are a way of measuring plant maturity.

General combining ability. The average or overall performance of a genetic strain in a series of crosses.

Genotype. The fundamental genetic constitution of an organism.

Germ. The embryo of the corn kernel. It contains most of the oil found in the kernel.

Grain. Comprises mature corn kernels produced by commercial growers for purposes other than growing or reproducing the species.

Grain parent. Male sterile, elite hybrid that comprises a large majority of the plants in the TOPCROSS® grain production system.

Grain Parent Seed. Corn seed used to produce grain parent plants.

Grain Quality Trait. This is any attribute of grain that is of commercial value. Such traits relate to the intermediate or final use of grain and include but are limited to the quantity or quality of oil, protein, starch, pigmentation, and fiber found in corn grain. Such traits also encompass physical attributes of the grain itself, such as grain texture, size, or hardness, among others. Certain of these compositional or physical attributes of grain correlate with functional attributes as well which are of commercial importance, such as susceptibility to breakage and spoilage, among others.

Heterozygous. A genetic condition existing when different alleles reside at corresponding loci on homologous chromosomes.

High oil source. A population of corn plants containing high oil genes used for corn breeding.

Homozygous. A genetic condition existing when identical alleles reside at corresponding loci on homologous chromosomes.

Hybrid. (1) The progeny of a cross fertilization between parents belonging to different genotypes. (2) The first generation offspring of a cross between two individuals differing in one or more genes.

Hybrid Vigor. The phenomenon in which the cross of two stocks produce hybrids that show increased vigor-heterosis compared to the parent stocks.

Inbred. A substantially homozygous individual, variety or line.

Inbred Line. (1) A line produced by continued inbreeding. In plant breeding a nearly homozygous line usually originating by continued self-fertilization, accompanied by selection. (2) A relatively homozygous line produced by inbreeding and selection.

Kernel. The corn caryopsis comprising a mature embryo and endosperm which are products of double fertilization.

Line. A group of individuals from a common ancestry. A more narrowly defined group than a variety.

Male Sterility. A condition in which pollen is absent or non-functional in flowering plants.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Moisture. The moisture is the actual percentage moisture of the grain at harvest.

Ovule: A structure consisting of female reproductive tissue surrounded by maternal tissue.

Pedigree. A record of the ancestry of an individual, family, or strain.

Pedigree Breeding. A system of breeding in which individual plants are selected in the segregating generations from a cross on the basis of their desirability and on the basis of a pedigree record.

Percent Oil. The oil concentration of a corn kernel expressed on a dry weight basis.

Percent Yield. The yield obtained for a hybrid in terms of percent of the mean for the experiments in which it was grown.

Phenotype. (1) Physical or external appearance of an organism as contrasted with its genetic constitution (=genotype). (2) A group of organisms with similar physical or external makeup. (3) The observed character of an individual without reference to its genetic nature.

Plant Height. This is a measure of the height of the hybrid from the ground to the tip of the tassel and is measured in centimeters. The data is given in percentage of mean of the experiments in which the hybrid was grown.

Polar Nuclei. Found in the ovule to give rise to the embryo and endosperm of the mature corn kernel.

Pollen. A structure which contains the two haploid sperm nuclei which fuse with the egg nucleus and polar nuclei found in the ovule to give rise to the embryo and endosperm of the mature corn kernel.

Pollinators. Male fertile corn plants that are used to pollinate male sterile hybrid corn plants.

Pollinator Seed. Corn seed that, when sown, germinates to produce pollinator plants.

Population. In genetics, a community of individuals which share a common gene pool. In statistics, a hypothetical and infinitely large series of potential observations among which observations actually made constitute a sample.

Recurrent Parent. Used in backcrosses to refer to the parent to which the first cross and successive backcrossed plants are crossed.

Seed. Mature corn kernels produced for the purpose of propagating the species.

Seed parent. A corn line that is pollinated by pollen from pollinator plants, with hybrid corn seed resulting from this pollination.

Seedling Vigor. This is the visual rating (1 to 5) of the amount of vegetative growth after emergence at the seedling stage (approximately five leaves). A higher score indicates better vigor.

Single Cross: A cross between two genotypes, usually genetically different inbred lines or synthetic lines.

Stay Green. Stay green is the measure of plant health near the time of black layer formation (physiological maturity). A low score on a scale of 1 to 5 indicates better late-season plant health.

Synthetic Hybrid. Any offspring of a cross between two genetically unlike synthetic individuals or unlike individuals.

Synthetic Population. A genetically heterogeneous collection of plants of known ancestry created by the intermating of any combination of inbreds, hybrids, varieties, populations, races or synthetics.

Synthetic Variety. A variety produced by crossing inter se a number of genotypes selected for good combining ability in all possible hybrid combinations, with subsequent maintenance of the variety by open pollination.

Test Cross. A cross of a double or multiple heterozygote to the corresponding multiple recessive to test for homozygosity or linkage.

Test Weight. The measure of the weight of the grain in pounds for a given volume (eg. bushel), adjusted for percent moisture.

TC BLEND®. A trademark of E.I. du Pont de Nemours and Company for corn seed for agricultural purposes.

TOPCROSS®. A trademark of E.I. du Pont de Nemours and Company for high oil corn seed.

TOPCROSS® Grain Production System. A method of commercial corn production whereby a low yielding male fertile corn pollinator is blended at 8 to 20% of the total seed count with an elite high yielding male sterile hybrid grain parent and allowed to pollinate the male sterile grain parent to produce grain having increased food and feed nutritional value, thus capitalizing on the high yield potential of the male sterile hybrid grain parent while contributing the grain quality traits from the fertile pollinator.

Variety. A subdivision of a species. A group of individuals within a species which are distinct in form or function from other similar arrays of individuals.

Yield (Bushels/Acre). The yield in bushels/acre is the actual yield of the grain at harvest adjusted to 15.5% moisture.

DETAILED DESCRIPTION OF THE INVENTION

P89 is a yellow dent corn, high oil single cross synthetic hybrid having superior agronomic characteristics and the ability to impart desirable grain quality traits to a first generation grain when used as a pollinator in the TOPCROSS® grain production system.

Synthetic hybrid P89 is produced by planting synthetic populations P90A and P91B, allowing one synthetic to pollinate the other, and harvesting the resulting seed. Either synthetic parental population may be used as the female parent or the male parent. Preferably, synthetic P91B is the female of the cross and synthetic P90A is the male of the cross because of the larger seed size grade-out resulting from the P91B seed parent in hybrid synthetic production. Production planting of the male and female synthetics can be made at the same time due to the fact that male pollen is shed at the same time the female silks are receptive to the pollen.

Parental lines P90A and P91B were produced by mass selection for later maturity flowering dates for two successive generations from P44A-Reid and P48B-Lancaster synthetic populations respectively. For each parental line, five hundred plants out of a stand of 20,000 were selected for late flowering date and desirable plant phenotype. Seed from these five hundred plants was grown out and the resulting plants were random mated by single plant sibbing. Late flowering plants from this second generation were selected, grown out, and random mated to develop P90A and P91B.

Mass selection of this type has proven effective in increasing the gene frequencies for later date maturity while maintaining the high oil gene frequencies necessary for pollinators in the TOPCROSS® grain production system. It has been found that flowering date may be advanced by approximately one day per each cycle of selection. Mass selection has thus been successful in developing later maturing pollinators for special late season TC Blends adapted to fit the new fuller season production areas of the United States and South American cornbelts.

P44A-Reid and P48B-Lancaster were produced by conducting a series of crosses, selfings and backcrosses beginning with the crossing of LH132 and B73 with ASKC28 and B73 with UHOC3 (for P44A-Reid) and the crossing of NC286 with ASKC28 (for P48B-Lancaster). During the random mating generation of development of P44A-Reid and P48B-Lancaster, test crosses were made to a hybrid grain parent tester and the resulting grain was analyzed to identify normal grain type segregate with favorable dominant oil genes expressing high oil in the genetic segregants.

When produced according the method summarized above, both P90A and P91B breed true, that is, produce a P89 synthetic hybrid that is both reproducible and usable as a high oil pollinator in the TOPCROSS® grain production system.

CHARACTERISTICS OF P89

Synthetic corn hybrid P89 most closely resembles synthetic corn hybrids LP57.1 and P66 in characteristics such as of plant type, ear type, kernel type and usage, but P89 is later in maturity.

P89 synthetic hybrid has the following characteristics, based on data primarily collected at Applicant's El Paso, Ill. research facility (numerical values given are averages taken across a fifty plant sample):

TABLE 1

SYNTHETIC HYBRID P89 DESCRIPTION INFORMATION

| | |
|---|---|
| Type: | Dent/High Oil |
| Region Best Adapted: | Most Central, Southern and Eastern Regions of USA Cornbelt |
| A. Maturity: | Zone 3–4 |
| Heat Units from Emergence to Shed: | 1150 GDD (1998) |
| Heat Units from Emergence to Silk: | 1174 GDD (1998) |
| Heat Units from 50% Silk to 25% Kernel Moisture: | 1404 GDD (1998) |
| Heat Units from Emergence to 25% Kernel Moisture: | 2662 GDD (1998) |
| No. Reps.: | 8 |
| Where Heat Units* = [(Max. Temp. (<86 Degrees F.) + Min. Temp. (>50 Degrees F.)) / 2] − 50 | |
| B. Plant Characteristics: | |
| Height (to tassel tip): | 263 cm |
| Length of Top Ear Internode: | 20 cm |
| Number of Ears per Stalk: | Slight two-ear tendency |
| Ear Height (to base of top ear): | 96 cm |
| Number of Tillers: | Mostly none, occasional one |
| Cytoplasm Type: | Normal |
| Brace Root Color: | Green |
| Number of Brace Root Nodes: | 2, slight three-node tendency |
| Number of Brace Roots: | 22 |
| Stalk: | Straight |
| C. Leaf: | |
| Color: | Green |
| Stalk Color: | Green |
| Angle from Stalk: | 64 Degrees |
| Attitude of Blade: | Slightly curved |
| Marginal Waves (number): | 2–3, few |

TABLE 1-continued

SYNTHETIC HYBRID P89 DESCRIPTION INFORMATION

| | |
|---|---|
| Number of Leaves (mature plants): | 13 |
| Sheath Pubescence: | Smooth, segregating for smooth and pubescence |
| Color of Sheath: | Pale green |
| Longitudinal Creases: | Absent |
| Length (Ear node leaf): | 81 cm |
| Width (widest point, ear node leaf): | 10 cm |
| Coleoptile Sheath Color: | Mostly green with a few purple |
| First Leaf, Shape of Tip | Round |
| D. Tassel: | |
| Attitude of Lateral Branches: | Mostly straight, segregating for curved |
| Number Lateral Branches: | 15 |
| Length of Lateral Branches: | 25 cm |
| Branch Angle from Central Spike: | 52 degrees |
| Length of Main Axis Above Lowest Branch: | 42 cm |
| Length (from flag leaf): | 53 cm |
| Peduncle Length (flag leaf to basal branches): | 11 cm |
| Anther Color: | Yellow |
| Glume Color: | Green |
| Density of Spikelets: | Medium |
| E. Ear (Husked Ear Data Except When Stated Otherwise): | |
| Length: | 18 cm |
| Weight (dried to 15.5% grain moisture): | 177 gm |
| Mid-point Diameter: | 4 cm |
| Silk Color (at silking): | Pale green |
| Husk Extension (Harvest stage): | Short, 6 cm (ear tip occasionally exposed) |
| Husk Leaf (number): | 7 |
| Husk Leaf Length: | 7 cm |
| Number of Husks: | 13 |
| Taper of Ear: | Average taper |
| Position at Dry Husk Stage: | Upright |
| Kernel Rows: | 18; Distinct, straight |
| Husk Color (fresh): | Light green |
| Husk Color (dry): | Buff |
| Shank Length: | 18 cm long |
| Shank (No. of internodes): | 11 |
| Drying Time (unhusked ear): | Average |
| Husk Length: | 28 cm |
| Husk Width: | 16 cm |
| Husk Area: | 468 cm$^2$ |
| F. Kernel (dried, size from ear mid-point): | |
| Length: | 12 mm |
| Width: | 7 mm |
| Thickness: | 4 mm |
| Shape Grade (% rounds): | 29% (±3%) based on parent test |
| Pericarp Color: | Colorless |
| Aleurone Color: | Homozygous; yellow |
| Cap Color: | Yellow |
| Endosperm Color: | Yellow |
| Endosperm Starch Type: | Normal starch, heterozygous for wx-gene |
| Gm Wt/100 Seeds (unsized): | 22 gm |
| Test Weight: | 56 lbs./bu. |
| Percent Oil: | 15.65% (1998) |
| Percent Protein: | 13.70% (1998) |
| Percent Starch: | 53% (1998) |
| Density: | 1.19 gm/ml (1998) |
| G. Cob (dried, size from ear mid-point): | |
| Diameter at mid-point: | 27 mm |
| Strength: | Strong |
| Color: | Red |
| H. Diseases: | |
| Northern Leaf Blight: | Intermediate, Ht Resistant Gene |
| Goss's Bacterial Wilt: | Intermediate |
| Southern Corn Leaf Blight: | Susceptible |
| Heat Smut: | Susceptible |
| Common Smut: | Resistant |
| Stewart's Bacterial Wilt: | Intermediate |
| Corn Lethal Necrosis: | Susceptible |
| Northern Leaf Spot: | Intermediate |
| Common Northern Rust: | Intermediate |
| Southern Rust: | Susceptible |
| Eye Spot: | Intermediate |
| Gray Leaf Spot: | Susceptible |
| Fusarium Ear Rot: | Resistant |
| Fusarium Stalk Rot: | Intermediate |
| Diplodia Ear Rot: | Susceptible |
| Diplodia Stalk Rot: | Intermediate |
| MDMV: | Susceptible |
| Stunt: | Susceptible |
| Stay Green: | Intermediate |
| I. Insects: | |
| European Corn Borer: | Susceptible |
| J. Variety most closely resembling: | |
| Character | Synthetic Hybrid |
| Maturity | P66 |
| Plant Type | LP57.1, P66 |
| Ear Type | LP57.1, P66 |
| Kernel Type | LP57.1, P66 |
| Usage | LP57.1, P66 |

*If Max. Temp. is greater than 86 degrees Fahrenheit, then 86 is used and if Min. Temp. is less than 50, then 50 is used. Heat units accumulated daily and can not be less than 0.

P89 is adapted over a wide area of the central and southern corn belt and can be used advantageously as a pollinator in seed blends with male sterile hybrids from approximately 96–100 relative maturity based on the Minnesota Relative Maturity Rating System for harvest moisture of the grain. In comparison tests done in 1998 at Applicant's El Paso, Ill. nursery, P89 required 1306.0 GDD from planting to tassel (72 calendar days) compared to 1294.5 GDD (71 calendar days) for P66 and 1251.1 GDD (69 calendar days) for LP57.1. In that same comparison P89 exhibited 15.65% oil in the grain versus 13.76% for P66 and 14.47% for LP57.1. P89 cold test vigor was excellent in laboratory tests, exhibiting 95% emergence compared to 93% emergence for LP57.1 and 95% emergence for P66. Kernel size-out is also very good for P89, with approximately 71% of the kernels falling in the medium flat category.

Although P89's primary use would be as a pollinator in the TOPCROSS® grain production system with blends of medium-late maturing corn hybrid male sterile grain parents, P89 is also an acceptable male to be crossed to later maturing full season high oil pollinators to develop late maturity pollinators for expanding the use of its genetics to fuller season maturity grain parents.

Pollen production is good with P89. Under extreme heat and drought stress, P89 may top fire and have some tassel blasting (necrosis of top leaves and tassel, respectively). P89 sheds pollen for approximately twenty days (Table 3) and should be blended in sufficient concentrations (at approximately 8–10% pollinator seed to 90–92% male sterile hybrid grain parent seed) to ensure adequate pollen in commercial production of high oil corn grain where it is used as a male pollinator.

As a pollinator, P89 has shown uniformity and stability within the limits of environmental influence for the grain traits of yield, moisture, oil concentration, protein concentration and test weight as shown in Table 2. P89 has not expressed segregation for red and white cob color because of the red cob genetics of P90A and P91B synthetic parent populations. P89 is a synthetic hybrid that has been maintained by hand and cross pollination in isolated fields with continued observation of high oil for uniformity of dominant high oil genetics. Although segregating for plant height in test crosses, P89 synthetic has consistently expressed high oil across different environments.

P89 is a medium-late maturity flowering synthetic hybrid, broadly adapted to the corn growing areas of the Central and Southern United States. P89 has expressed high oil and excellent cold soil seedling vigor that conditions low grain moisture in the grain of male sterile hybrid grain parents.

BENEFITS OF P89 AS A POLLINATOR

In field tests of the TOPCROSS® grain production system using P89 as the pollinator and a male sterile hybrid grain parent, P89 was found to induce superior grain quality characteristics in grain arising on the male sterile hybrid.

In field tests, P89 and male sterile grain parent plants were allowed to grow unmolested to maturity. Both varieties were allowed to continue to grow and natural cross-pollination was allowed to occur by the action of the wind as is normal with most grasses, including corn. Of course, only pollen from the fertile male parent, P89, was available for pollination of the male sterile hybrid grain parent; the tassels, or flower bearing parts, of the grain parent having been rendered sterile by genetic/cytoplasmic mechanisms For convenience, the grain harvested from the male sterile grain parent plants and the P89 plants will hereinafter be referred to as "high oil corn grain."

The fields where high oil corn grain was produced were well isolated from other corn fields to prevent any accidental contamination with ambient pollen. Such isolation techniques may be accomplished by timed delay with other hybrid corn production fields or by using a space distance pattern of more than 70 m from normal corn, well known to those skilled in the art of the seed corn industry.

Both the male fertile pollinator and male sterile hybrid grain parent varieties comprising the corn seed blend were allowed to continue to grow and be harvested. The ears harvested from the male sterile grain parent expressed the higher grain yield potential of the elite male sterile grain parent and the high oil and grain density qualities of the pollen parent. The grain from the male parent variety ears may be harvested along with the grain of male sterile grain parent for high oil corn use.

Because the same oil source (i.e. ASKC28) was used in the development of the P90A-Reid and P91B-Lancaster parental populations, only modest heterotic effects for yield were expressed in P89. The low grain yields expected from synthetic hybrid P89 pollinator dictated the need for a low percent of pollinator in the pollinator-grain parent seed blend so as to maximize yield, but a high enough percent was needed to ensure sufficient pollination of the elite male sterile grain parent hybrid.

EXAMPLES OF USING P89 AS A POLLINATOR

In the examples that follow, the characteristics of high oil corn grain produced using P89 as a pollinator are provided.

1998 Strip Test Trials

First year (1998) strip tests trials were conducted at El Paso, Ill., comparing the characteristics of grain from various hybrids from Pfister Hybrid Corn Company and Pioneer Hi-Bred International rendered male sterile and pollinated by P89, with characteristics of grain produced from grow outs of the same Pfister and Pioneer hybrids in their fertile state ("Hybrid Self"). The hybrids used were Pioneer Hybrid P32R90 and Pfister Hybrids 2065, 2652, 2660, 2680, 3001, 3049, 3977, X696, X701 and X783. The results are presented in Table 2.

For convenience, the grain harvested from the male sterile grain parent plants and the P89 plants will hereinafter be referred to as "high oil corn grain."

TABLE 2

1998 P89 Strip Tests Results - El Paso, Illinois

| Hybrid Grain Parent | GDD | Grain Yield-Bu/A. | | | Moisture Percent | | | Oil Percent | | | Protein Percent | | | Test Weight (lbs./bu.) | | |
|---|---|---|---|---|---|---|---|---|---|---|---|---|---|---|---|---|
| | | Top-Cross | % of GP | Hybrid GP Self | Top-Cross | % of GP | Hybrid GP Self | Top-Cross | % of GP | Hybrid GP Self | Top-Cross | % of GP | Hybrid GP Self | Top-Cross | % of GP | Hybrid GP Self |
| Pioneer P32R90-Sdms | 1329 | 126.0 | 76 | 166.7 | 21.8 | 107 | 20.3 | 7.22 | 177 | 4.08 | 9.7 | 96 | 10.1 | 54.8 | 91 | 60.3 |
| Pfister 2650-Sdms | 1199 | 162.3 | 91 | 173.7 | 18.0 | 119 | 15.1 | 6.40 | 164 | 3.89 | 8.7 | 99 | 8.8 | 52.0 | 88 | 58.8 |
| Pfister 2652-Sdms | 1249 | 158.8 | 92 | 172.3 | 18.5 | 104 | 17.7 | 6.95 | 162 | 4.28 | 8.8 | 101 | 8.7 | 51.0 | 88 | 57.6 |
| Pfister 2660-Sdms | 1222 | 135.2 | 82 | 163.9 | 19.9 | 105 | 19.0 | 7.00 | 170 | 4.11 | 8.8 | 105 | 8.4 | 48.6 | 86 | 56.4 |
| Pfister 2680-Sdms | 1189 | 126.2 | 69 | 183.9 | 20.9 | 100 | 20.9 | 7.57 | 209 | 3.62 | 8.2 | 92 | 8.9 | 50.6 | 87 | 58.4 |
| Pfister 3001-Sdms | 1213 | 108.7 | 67 | 161.6 | 20.4 | 102 | 20.0 | 8.38 | 209 | 4.01 | 8.7 | 93 | 9.3 | 50.8 | 91 | 55.7 |
| Pfister 3049-Sdms | 1219 | 135.1 | 73 | 183.9 | 21.4 | 111 | 19.2 | 7.35 | 164 | 4.47 | 8.9 | 102 | 8.7 | 50.4 | 89 | 56.3 |
| Pfister 3977-Sdms | 1222 | 149.6 | 78 | 191.4 | 25.0 | 120 | 20.8 | 7.55 | 177 | 4.27 | 8.6 | 105 | 8.2 | 49.0 | 86 | 56.7 |
| Pfister X696-Sdms | 1263 | 130.3 | 76 | 170.6 | 24.2 | 114 | 21.2 | 9.64 | 157 | 6.15 | 8.9 | 95 | 9.4 | 52.2 | 85 | 61.1 |
| Pfister X701-Sdms | 1094 | 131.3 | 73 | 179.4 | 16.1 | 76 | 21.1 | 8.11 | 177 | 4.59 | 8.8 | 99 | 8.9 | 52.2 | 91 | 57.1 |
| Pfister X783-Sdms | 1252 | 112.3 | 66 | 170.8 | 19.6 | 105 | 18.7 | 8.83 | 150 | 5.87 | 9.2 | 107 | 8.6 | 52.2 | 87 | 60.2 |
| Overall Mean | | 134.2 | 77 | 174.4 | 20.5 | 106 | 19.4 | 7.73 | 172 | 4.49 | 8.8 | 99 | 8.9 | 51.2 | 88 | 58.0 |

NOTE:
"TopCross" as used in this table refers to grain resulting from the pollination by P89 of both the male sterile hybrid grain parent and P89.

NOTE: "TOPCROSS" as used in this table refers to grain resulting from the pollination by P89 of both the male sterile hybrid grain parent and P89.

Traits obtained from the strip test include the following:

"Grain yield", expressed in bushels per acre for both the grain produced by the pollination of the male sterile grain parent hybrid by P89 and the grain produced from the grow out of the fertile hybrid.

"Moisture Percent", expressed as a percentage of total kernel weight for both grain produced from the pollination of the male sterile hybrid by P89 and for the grow out of the fertile hybrid. Moisture percent was determined by distillation on a Brown-Duvel moisture tester manufactured by the Seed Trade Reporting Bureau of Chicago, Ill. Electronic moisture testers were calibrated against the moisture determinations of the Brown-Duvel moisture tester in field harvest tests.

"Oil Percent", expressed as a percentage of the total kernel dry weight for both grain produced from the pollination of the male sterile hybrid by P89 and for the grow out of the fertile hybrid. Thus oil percent is a measure of the content of oil in grain at harvest. Oil percent was determined by NIR on a dry matter basis (0% moisture).

"Protein Percent", expressed as a percentage of protein in the grain on a dry matter basis as determined by NIR for both grain produced from the pollination of the male sterile hybrid by P89 and for the grow out of the fertile hybrid.

"Test Weight", expressed as the weight of the grain in pounds for a given volume (bushel) adjusted for percent moisture for both grain produced from the pollination of the male sterile hybrid by P89 and for the grow out of the fertile hybrid.

Grain Yield Comparisons—High Oil Corn Grain Versus Hybrid Self

In the 1998 strip test trials (Table 2), blends of 8–9% pollinator seed and 91–92% male sterile hybrid seed were planted and grown to maturity. Grain from both the male sterile hybrid plants and the pollinator plants (i.e., high oil corn grain) was harvested.

As shown in Table 2, the overall mean yield of grain produced by the pollination of the male sterile hybrids by P89 during the first year (1998) strip tests was 77% of the overall mean yield of grain produced from the fertile grain parent grow outs in eleven comparisons. The relatively low yield of High Oil Corn grain compared to the selfed fertile grain parent was attributed to location effects and a bad spot in the field. This was also reflected in test weight results.

Moisture Comparisons—High Oil Corn Grain Versus Hybrid Self

Conventional high oil hybrids traditionally express higher grain moisture at harvest and are slower to dry down than lower-oil dent hybrids of the same maturity. To test this concept of higher moisture associated with higher oil content of grain, comparisons were made of moisture at harvest of grain resulting from the pollination by P89 of the male sterile hybrids and grain resulting from the self pollination of the comparable fertile hybrids.

In the first year (1998) trials (Table 2), the overall mean grain moisture at harvest from the sterile grain parent hybrids pollinated by P89 was higher than the grain moisture from the fertile grain parent hybrids alone in all six comparisons. Since higher oil content resulted in higher moisture content in all six comparisons, the first year data did support the conventional theory regarding the relationship between oil content and grain moisture.

Oil Comparisons—High Oil Corn Grain Versus Hybrid Self

In the first year (1998) strip tests at El Paso, Ill., the oil contents of grain produced from the pollination by P89 of the male sterile hybrids were compared to grain produced from the self pollination of the comparable fertile hybrids. The results, shown in Table 2, show a consistent increase in oil percent in the high oil corn grain compared to the hybrid selfs. To take but two examples, there was about a 3.14% absolute increase in oil when Pioneer Hybrid P32R90 was pollinated by P89 (7.22% versus 4.08%), and about a 3.95% absolute increase in oil when Pfister Hybrid 2680 was pollinated by P89 (7.57% versus 3.62%).

Protein Comparisons—High Oil Corn Grain Versus Hybrid Self

In first year (1998) strip tests (Table 2), protein content of the grain resulting from the pollination of the male sterile hybrid by P89 was compared to the protein content of grain produced from open pollinated fertile hybrid checks and found to be about the same. The fact that the high oil corn grain did not exhibit higher protein than that of the fertile grain parent hybrid checks may have been due to a lower level of nitrogen in the field.

Test Weight Comparisons—High Oil Corn Grain Versus Hybrid Self

Test weight of grain is a function of kernel density. In first year strip tests, comparisons were made of the test weight of high oil corn grain resulting from the pollination by P89 of male sterile hybrids against the test weight of grain resulting from the self pollination of the comparable fertile hybrids. As shown in Table 2, the overall mean test weight of high oil corn grain was 51.2 lbs./Bu., or 88% of the mean test weight of the selfed hybrids (58.0 lbs./bu.).

P89 conditions a slight loss in test weight in the high oil corn grain which is reflected in a slight yield penalty. This is because P89 was developed by crossing P90A-Reid, a soft starch grain phenotype, with P91B-Lancaster, a normal starch grain phenotype. This cross yields a heterogeneous condition in the P89 pollinator, i.e., the presence of different types of male pollen gametes—soft starch and normal starch. When P89 is used as a pollinator, the two types of male pollen gametes fertilize the male sterile hybrid grain parent. As a result, some of the high oil corn grain expresses lower test weight (female ovules fertilized by male gametes with soft starch genotype) and the remainder of the grain expresses normal test weight (female ovules fertilized by male gametes with normal starch genotype). Overall, the grain exhibits a mid-parent mean that results in a slight loss in test weight which is reflected in a slight yield penalty.

Tassel-Silk Synchronization—P89 Pollen Shed and Grain Parent Silk Extrusion

The success of the TOPCROSS® grain production system is dependent on the synchronization of pollen shed from the pollinator with the extrusion of silks from the male sterile grain parent hybrid, which is termed nicking.

Table 3 presents results of tassel-silk date observations and growing degree days (GDD) to tassel shed and silk flowering for P89 pollinator and Pfister Hybrid 3049, respectively. As shown in the table, in 1998 strip tests the pollination period of P89 began July 12 and ended July 31, a twenty (20) day period. Peak pollination, i.e., the date during which 50% pollen shedding was achieved, occurred on July 17 which resulted from an accumulation of 1150 GDD. By comparison, the peak silk extrusion date for Pfister Hybrid 3049 was slightly earlier—July 15— which resulted from an accumulation of 1103 GDD. These data indicate that the nicking of pollinator P89 with male sterile Pfister Hybrid 3049-Sdms is acceptable for commercial high oil corn grain production.

TABLE 3

Comparison of the Tassel Shedding Period for P89
with the Silk Extrusion Period for Pfister Hybrid 3049
Total Plants Observed - 121
1998 Field Test Data

| Date | July 12 | July 13 | July 14 | July 15 | July 16 | July 17 | July 18 | July 19 | July 20 | July 21 |
|---|---|---|---|---|---|---|---|---|---|---|
| Percent of Pollinator P89 to Start Shedding | 2 | 2 | 9 | 7 | 20 | 17 | 12 | 5 | 11 | 6 |
| Percent of Pollinator P89 to Stop Shedding | | | | | | | 2 | 3 | 12 | 28 |
| Percent of Hybrid 3049 to Begin Silk Extrusion | 1 | | 2 | 8 | 13 | 21 | 11 | 7 | 15 | 10 |
| Growing Degree Days | 1036 | 1058 | 1082 | 1103 | 1128 | 1150 | 1174 | 1201 | 1226 | 1255 |

| Date | July 22 | July 23 | July 24 | July 25 | July 26 | July 27 | July 28 | July 29 | July 30 | July 31 |
|---|---|---|---|---|---|---|---|---|---|---|
| Percent of Pollinator P89 to Start Shedding | 3 | 3 | 1 | 2 | | | | | | |
| Percent of Pollinator P89 to Stop Shedding | 12 | 6 | 11 | 4 | 4 | 11 | 2 | 2 | 1 | 2 |
| Percent of Hybrid 3049 to Begin Silk Extrusion | 4 | 5 | | 2 | 1 | | | | | |
| Growing Degree Days | 1276 | 1297 | 1313 | 1329 | 1346 | 1362 | 1386 | 1409 | 1430 | 1445 |

Comparisons of Oil, Protein and Moisture in Grain Produced from Hybrids Pollinated by P89 and Self Pollinated Fertile Hybrids Harvested Over Time Table 4 presents the oil content, protein content and moisture of grain produced from Pfister Hybrids 3049 and 3049-Sdms (columns one and two), grain produced from Pfister Hybrids 3049 and 3049-Sdms pollinated by P89 (columns three and four), and grain produced from self-pollinated P89 (column five) when the grain was harvested 37 days after flowering and then harvested on selected days to and beyond the onset of physiological maturity (i.e., black-layer).

Pfister Hybrid 3049-Sdms pollinated by P89 expressed 6.8% oil content of the grain as early as 786 GDD after flowering, thus indicating a very high level of oil while the plant foliage was green and actively growing. This permits an early harvest for silage and/or earlage while maintaining a high energy recovery from the grain.

A comparison of the protein content data shows only a slight increase in protein at 37 days after flowering through 69 days, suggesting the physiological make-up of the seed is basically complete at the early harvest date.

A comparison of moisture over the course of 33 days (i.e., August 24 to September 25) illustrates the rate of dry down. The moisture data indicates there were no major grain moisture differences between grain resulting from the self-pollination of fertile hybrid 3049 (column one) to grain resulting from the pollination by P89 of male sterile hybrid 3049-Sdms (column four).

TABLE 4

Percent Oil, Protein and Moisture of Grain at Harvest Across Days Commencing 37 Days After Pollination
Through 69 Days After Pollination of Five Corn Types (1998)

| | | (1) Pfister 3049 | | | (2) Pfister 3049-Sdms | | | (3) Pfister 3049 and P89 | | | (4) Pfister 3049-Sdms and P89 | | | (5) P89 | | | GDD from Flowering |
|---|---|---|---|---|---|---|---|---|---|---|---|---|---|---|---|---|---|
| (A) | (B) | Oil | Protein | Moist | Oil | Protein | Moist | Oil | Protein | Moist | Oil | Protein | Moist | Oil | Protein | Moist | to Harvest |
| 8/24 | (37) | 4.0 | 9.6 | 42.3 | 3.9 | 9.8 | 43.1 | 7.0 | 10.2 | 41.2 | 6.8 | 8.8 | 42.0 | 14.1 | 15.8 | 46.1 | 786.0 |
| 8/27 | (40) | 3.8 | 10.4 | 41.5 | 3.9 | 9.7 | 41.1 | 7.4 | 9.4 | 40.4 | 7.0 | 10.0 | 41.8 | 13.6 | 15.3 | 44.1 | 856.5 |
| 9/1 | (45) | 4.4 | 9.0 | 35.8 | 4.3 | 9.4 | 36.6 | 7.2 | 9.6 | 38.0 | 7.1 | 10.2 | 38.8 | 13.7 | 13.2 | 44.9 | 957.0 |
| 9/7 | (51) | 4.0 | 11.3 | 30.4 | 4.2 | 9.6 | 31.2 | 7.0 | 9.7 | 32.9 | 6.9 | 9.1 | 33.3 | 14.6 | 13.8 | 37.8 | 1085.5 |
| 9/8 | (52) | | | * | | | * | | | * | | | * | | | * | 1098.5 |
| 9/11 | (55) | 4.3 | 10.3 | 26.6 | 4.0 | 9.5 | 27.4 | 8.1 | 7.5 | 25.8 | 7.0 | 10.2 | 30.5 | 13.5 | 15.2 | 33.1 | 1145.5 |
| 9/17 | (60) | 4.6 | 9.2 | 25.6 | 4.2 | 11.1 | 26.5 | 7.1 | 9.4 | 24.1 | 7.0 | 9.8 | 28.0 | 14.1 | 14.2 | 30.7 | 1265.0 |
| 9/21 | (65) | 4.3 | 9.1 | 20.9 | 4.1 | 9.9 | 21.8 | 7.1 | 8.1 | 19.0 | 7.1 | 10.1 | 22.8 | 14.1 | 13.1 | 31.7 | 1351.0 |

TABLE 4-continued

Percent Oil, Protein and Moisture of Grain at Harvest Across Days Commencing 37 Days After Pollination Through 69 Days After Pollination of Five Corn Types (1998)

| | | (1) Pfister 3049 | | | (2) Pfister 3049-Sdms | | | (3) Pfister 3049 and P89 | | | (4) Pfister 3049-Sdms and P89 | | | (5) P89 | | | GDD from Flowering |
|---|---|---|---|---|---|---|---|---|---|---|---|---|---|---|---|---|---|
| (A) | (B) | Oil | Protein | Moist | Oil | Protein | Moist | Oil | Protein | Moist | Oil | Protein | Moist | Oil | Protein | Moist | to Harvest |
| 9/25 | (69) | 4.4 | 10.0 | 22.2 | 4.3 | 10.1 | 21.2 | 7.3 | 11.9 | 21.5 | 7.2 | 10.1 | 22.2 | 13.8 | 14.0 | 24.5 | 1404.0 |
| MEAN | | 4.2 | 9.9 | 30.7 | 4.1 | 9.9 | 31.1 | 7.3 | 9.5 | 30.4 | 7.0 | 9.8 | 32.4 | 13.9 | 14.3 | 36.6 | 1105.0 |

(A) = Harvest Date
(B) = Days After Pollination
*Date of black layer, physiological maturity.

DEPOSIT INFORMATION

Applicant has made available to the public without restriction a deposit of at least 2500 seeds of synthetic hybrid P89, at least 2500 seeds of P90A-Reid, and at least 2500 seeds of P91B-Lancaster, with the American Type Culture Collection (ATCC), 10801 University Boulevard, Manassas, Va. 20110-2209. The depositor was Optimum Quality Grains, L.L.C. The date of the deposits was Jun. 4, 1999. P89 was assigned ATCC Accession No. PTA-174. P90A was assigned ATCC Accession No. PTA-175. P91B was assigned ATCC Accession No. PTA-176. The viabilty of the seeds was tested on Jun. 14, 1999. On this date, the seeds were viable and capable of reproduction.

The seeds deposited with the ATCC were taken from the same deposits maintained by Optimum Quality Grains, L.L.C., Box 19, 90 North Fayette Street, El Paso, Ill. 61738, since prior to the filing date of this application. The deposits will be maintained in the ATCC depository, which is a public depository, for a period of 30 years, or 5 years after the most recent request, or for the enforceable life of the patent, whichever is longer, and will be replaced if they become nonviable during that period.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed is:

1. A synthetic hybrid corn seed designated P89, a representative sample of which has been deposited under ATCC Accession No. PTA-174.

2. A synthetic hybrid corn plant or its parts produced by the seed of claim 1.

3. Pollen of the synthetic hybrid corn plant of claim 2.

4. A tissue culture comprising regenerable cells of the synthetic hybrid corn plant of claim 2.

5. A corn plant regenerated from the tissue culture of claim 4, wherein said plant has all the physiological and morphological characteristics of P89.

6. A synthetic hybrid corn plant having all the physiological and morphological characteristics of the synthetic hybrid corn plant P89, ATCC Accession No. PTA-174.

7. A method for producing a synthetic hybrid corn seed designated P89, ATCC Accession No. PTA-174, comprising the steps of:

a) planting in pollinating proximity seeds of corn synthetic lines P90A, ATCC Accession No. PTA-175, and P91B, ATCC Accession No. PTA-176;

b) cultivating corn plants resulting from the planting until the time of flowering;

c) emasculating the flowers of the plants of either synthetic line P90A or P91B;

d) allowing cross pollination to occur between the synthetic lines; and e) harvesting seeds produced on the emasculated plants of the synthetic line.

8. A synthetic hybrid corn plant produced by crossing P89, ATCC Accession No. PTA-174, with another, different corn plant, the resulting progeny having one half of the nuclear genotype of P89.

9. A seed corn blend comprising a mixture of male sterile hybrid corn seed and the synthetic hybrid corn seed of claim 1.

10. Corn grain produced by the process of:

(a) planting, in pollinating proximity, seeds of synthetic hybrid corn plant P89, ATCC Accession No. PTA-174, and seeds of a male sterile corn hybrid;

(b) cultivating corn plants resulting from the planting;

(c) allowing the P89 corn plants to pollinate the male sterile hybrid corn plants; and (d) harvesting the resulting corn grain from all plants.

11. A synthetic corn seed designated P90A and having ATCC Accession No. PTA-175.

12. A synthetic corn seed designated P91B and having ATCC Accession No. PTA-176.

13. A corn plant produced from a seed of claim 1 having the ability to impart desirable grain quality traits to a first generation grain when used as a pollinator in the TOPCROSS® grain production system.

14. A corn plant produced from a seed of claim 1 having the ability to impart a high oil level to a first generation grain when used as a pollinator in the TOPCROSS® grain production system.

15. A corn plant derived from a seed of claim 1 and retaining the ability to impart a high oil level to a first generation grain when used as a pollinator in the TOPCROSS® grain production system.

* * * * *